United States Patent
Kim et al.

(10) Patent No.: US 11,672,756 B2
(45) Date of Patent: Jun. 13, 2023

(54) TEMPERATURE SENSITIVE HYDROGEL COMPOSITION INCLUDING NUCLEIC ACID AND CHITOSAN

(71) Applicant: PharmaResearch Co., Ltd., Gangneung-si (KR)

(72) Inventors: Ik Soo Kim, Seongnam-si (KR); Han Gyu Kim, Wonju-si (KR); Cheol Am Hong, Daegu (KR); Su Yeon Lee, Seongnam-si (KR)

(73) Assignee: PHARMARESEARCH CO., LTD., Gangneung-si (KR)

( * ) Notice: Subject to any disclaimer, the term of this patent is extended or adjusted under 35 U.S.C. 154(b) by 528 days.

(21) Appl. No.: 16/075,296

(22) PCT Filed: Feb. 29, 2016

(86) PCT No.: PCT/KR2016/002013
§ 371 (c)(1),
(2) Date: Aug. 3, 2018

(87) PCT Pub. No.: WO2017/135498
PCT Pub. Date: Aug. 10, 2017

(65) Prior Publication Data
US 2019/0054015 A1  Feb. 21, 2019

(30) Foreign Application Priority Data

Feb. 5, 2016  (KR) .......................... 10-2016-0015112

(51) Int. Cl.
| | | |
|---|---|---|
| *A61K 9/00* | (2006.01) | |
| *A61K 47/36* | (2006.01) | |
| *C08J 3/075* | (2006.01) | |
| *C08L 5/08* | (2006.01) | |
| *C08L 5/00* | (2006.01) | |
| *A61K 31/7088* | (2006.01) | |

(52) U.S. Cl.
CPC ........ *A61K 9/0024* (2013.01); *A61K 31/7088* (2013.01); *A61K 47/36* (2013.01); *C08J 3/075* (2013.01); *C08L 5/00* (2013.01); *C08L 5/08* (2013.01); *C08J 2305/00* (2013.01); *C08J 2305/08* (2013.01); *C08J 2377/04* (2013.01); *C08J 2405/08* (2013.01)

(58) Field of Classification Search
CPC ................ C08L 5/00; C08L 5/08; C08J 3/075
See application file for complete search history.

(56) References Cited

U.S. PATENT DOCUMENTS

| 2015/0111834 A1 | 4/2015 | Cheng et al. |
| 2017/0326275 A1 | 11/2017 | Lecler et al. |
| 2019/0054015 A1 | 2/2019 | Kim et al. |

FOREIGN PATENT DOCUMENTS

| CN | 103848928 A | 6/2014 | |
| EP | 2745849 A1 | 6/2014 | |
| KR | 10-2012-0090746 A | 8/2012 | |
| KR | 10-2014-0090670 A | 7/2014 | |
| WO | 02/057424 A2 | 7/2002 | |
| WO | 2007/087350 A2 | 8/2007 | |
| WO | 2010/017264 A2 | 2/2010 | |
| WO | 2011/068774 A2 | 6/2011 | |
| WO | 2012148684 A1 | 11/2012 | |
| WO | WO-2013071235 A1 * | 5/2013 | ............... A61P 7/04 |
| WO | 2016/091778 A1 | 6/2016 | |

OTHER PUBLICATIONS

Ruel-Gariepy and Leroux, "In situ-forming hydrogels—review of temperature-sensitive systems" European Journal of Pharmaceutics and Biopharmaceutics, 2004, 58: 409-426 (Year: 2004).*
Zhou et al. Effect of molecular weight and degree of chitosan deacetylation on the preparation and characteristics of chitosan hermosensitive hydrogel as a delivery system, Carbohydrate Polymers, 2008, 73: 265-273 (Year: 2008).*
Amalik et al. Hyaluronic acid-coated chitosan nanoparticles: Molecular weight-dependent effects on morphology and hyaluronic acid presentation Journal of Controlled Release 172 (2013) 1142-1150 (Year: 2013).*
Lee et al. Thiolated Chitosan/DNA Nanocomplexes Exhibit Enhanced and Sustained Gene Delivery 2007 Pharmaceutical Research, vol. 24, No. 1: 157-167 (Year: 2007).*
Lee, J. I. et al., "DNA nanogels composed of chitosan and Pluronic with thermo-sensitive and photo-crosslinking properties", International Journal of Pharmaceutics, 2009, 373, 93-99.
Riva, R. et al., "Chitosan and Chitosan Derivatives in Drug Delivery and Tissue Engineering", Advances in Polymer Science, 2011, 244, 19-44.
Lee Jong-beom et al, "Nucleic Acid Nanotechnology", News & Information for Chemical Engineers, 2012, 30(5), 539-546.
Augst A.D. et al., Alginate hydrogels as biomaterials, Macromol. Biosci., 6(8), 623-633, 2006.
Berger J. et al., Structure and interactions in covalently and ionically crosslinked chitosan hydrogels for biomedical applications, Eur. J. Pharm. Biopham., 57(1), 19-34, 2004.

(Continued)

*Primary Examiner* — Taeyoon Kim
*Assistant Examiner* — Alexandra F Connors
(74) *Attorney, Agent, or Firm* — Rothwell, Figg, Ernst & Manbeck, P.C.

(57) ABSTRACT

The present invention provides a temperature sensitive hydrogel composition including a nucleic acid and chitosan. Since the hydrogel has excellent biocompatibility and biostability, and simultaneously has sol-gel phase transition properties depending on temperature changes, the hydrogel is present in a sol state at room temperature and becomes a gel when the hydrogel is injected into the human body or applied on the surface of epithelial skin and the temperature increases. Thus, the temperature-sensitive hydrogel of the present invention can be directly injected into and applied on certain parts requiring treatment and the retention and attaching time of a drug is increased through gelation depending on the temperature so that drug efficacy is sufficiently exhibited. Therefore, it is expected that the temperature-sensitive hydrogel of the present invention can be utilized for various treatments.

19 Claims, 2 Drawing Sheets

(56) References Cited

OTHER PUBLICATIONS

Bodugoz-Senturk H. et al., Poly(vinyl alcohol)-acrylamide hydrogels as load-bearing cartilage substitute, Biomaterials, 30(4), 589-596, 2009.
Hoffman A.S. et al., Hydrogels for biomedical applications, Advanced Drug Delivery Reviews, 43(1), 3-12, 2002.
Hwang Jun-seok et al., Research and Development of Superporous Hydrogels with Fast Swelling and Superabsorbent Properties, Tissue Engineering and Regenerative Medicine, 5(2), 147-155, 2008.
Jin R.H. et al., Fabrication of silver porous frameworks using poly (ethyleneimine) hydrogel as a soft sacrificial template, J. Mater. Chem., 15(42), 4513-4517, 2005.
Mahoney M.J. et al., Three-dimensional growth and function of neural tissue in degradable polyethylene glycol hydrogels, Biomaterials, 27(10), 2265-2274, 2006.
Park Jun-kyu et al., Thermosensitive Chitosan-based Hydrogel with Growth Factor as Adhesion Barrier, Polymer (Korea), 39(3), 480-486, 2015.
Rohindra D.R. et al., Swelling properties of chitosan hydrogels, The South Pacific Journal of Natural Science, 22(1), 32-35, 2004.
Um S.H. et al., Enzyme-catalysed assembly of DNA hydrogel, Nature Materials, 5(10), 797-801, 2006.
Ward M.A. et al., Thermoresponsive Polymers for Biomedical Applications, Polymers, 3(3), 1215-1242, 2011.
King Y. et al., Self-Assembled DNA Hydrogels with Designable Thermal and Enzymatic Responsiveness, Advanced Materials, 23(9), 1117-1121, 2011.
International Search Report and Written Opinion issued for PCT/KR2016/002013 dated Oct. 12, 2016, 7 pages.
Search Report issued for European Patent Application No. 16 889 476.4 dated Aug. 13, 2019, 8 pages.
Ishii-Mizuno Y, et al. "Improved sustained release of antigen from immunostimulatory DNA hydrogel by electrostatic interaction with chitosan", Int J Pharm. 2017; 516(1-2):392-400. doi: 10.1016/j.ijpharm.2016.11.048.
Lu et al., "Novel hyaluronic acid-chitosan nanoparticles as non-viral gene delivery vectors targeting osteoarthritis", International Journal of Pharmaceutics, 420, (2011) 358-365.

* cited by examiner (A)

(B)

TEMPERATURE SENSITIVE HYDROGEL COMPOSITION INCLUDING NUCLEIC ACID AND CHITOSAN

CROSS-REFERENCE TO RELATED APPLICATION(S)

The application is a 35 U.S.C. § 371 National Phase Entry Application from PCT/KR2016/002013, filed on Feb. 29, 2016, and designating the United States, which claims the benefit of priority to Korean Patent Application No. 10-2016-0015112, filed on Feb. 5, 2016, which is incorporated herein by reference in its entirety for all purposes.

TECHNICAL FIELD

The present invention relates to a temperature-sensitive hydrogel composition containing a nucleic acid and chitosan.

BACKGROUND ART

A hydrogel is a polymer structure having a three-dimensional network structure containing a water phase (Rohindra D. R. et al., 2004), and the hydrogel is formed by covalent binding or non-covalent binding between hydrophilic polymers (Hwang Jun Seok, et al., 2008). The hydrogel composed of various hydrophilic polymers has a high moisture content, leading to excellent biocompatibility, and thus many studies have been made for the application thereof as a biomaterial. Hydrogels sensitive to stimuli, such as pH, temperature, electric field, magnetic field, light, and ultrasonic waves, may be especially used in drug delivery systems allowing the controlled release according to the absence or presence of stimuli (Hoffman A. S., 2002).

Of these, temperature-sensitive hydrogels are most widely studied in cell carriers and drug delivery systems for tissue regeneration. The reason is that many polymers exhibit temperature transition characteristics. Therefore, when a hydrophilic group capable of dissolving or swelling general polymers in water is introduced, the corresponding polymers are dissolved or swollen in water and thus the solubility of the polymers in water increases as the temperature increases, but the polymers composed of a hydrophilic portion and a hydrophobic portion, such as methyl, ethyl, and propyl, have a lower critical solution temperature (LCST) at which the solubility in water decreases as the temperature increases, and thus the polymers are condensed to form a gel when the temperature increases (Ward M. A. et al., 2011). That is, a polymer composed of hydrophilic and hydrophobic portions is dissolved in water to become a sol state since the hydrogen bonding strength between the hydrophilic group of the polymer and a water molecule is strong, but when the temperature is increased, the binding strength between the hydrophobic group portions of the polymer is stronger than the hydrogen bonding strength, and thus the hydrophobic group portion of the polymer agglomerates to cause phase transition into a gel state.

In the case where this polymer solution is in a sol state, such as a fluid, at a general temperature, the mixing with a drug is allowable through simple mixing, and in the case where a heat having a temperature equal to or higher than the body temperature is applied to the polymer solution, the polymer solution forms a gel, allowing a sustained release of a drug. However, such a polymer needs to be released out of the human body through the metabolism of the human body after being used in the human body. Therefore, it is important that temperature-sensitive hydrogels for medical or human application exhibit biocompatibility and biodegradability.

As for the content of the temperature-sensitive hydrogel composition, which has been studied until now, it can be seen that the reaction concentrations of the compositions are higher in the temperature-sensitive hydrogels shown by hydrophobic-hydrophilic linkage. A high reaction concentration cannot only influence the human body by the injection of hydrogels into the human body, but also influence the degradation rates in the human body. Therefore, the development of hydrogels capable of exhibiting temperature sensitivity even at low concentrations can help developing safer biocompatible substances.

The polymers constituting hydrogels include: natural polymers, such as chitosan (Berger J. et al., 2004), alginate (Augst A. D. et al., 2006), dextran, hyaluronic acid, gelatin, and collagen; and synthetic polymers, such as poly(vinylalcohol) (Bodugoz-Senturk H., et al., 2009), polyethyleneimine (Jin R. H. et al., 2005), and polyethylene glycol) (Mahoney M. J. et al., 2006).

Chitosan may be produced by deacetylation of chitin, which is a natural polysaccharide in a β-(1→4)-linked form of N-acetyl-D-glucosamine that can be obtained from cellular walls of crustaceans, such as crab, general shrimp, and lobster; mollusks such as cuttlefish; insects; and bacteria. Chitosan is easily dissolved in an inorganic acid aqueous solution, and thus is utilized in various fields, such as coagulants for wastewater treatment, heavy metal adsorbents, foods, and cosmetics. In addition, chitosan is a polysaccharide obtained from natural materials, and it has been reported that chitosan has excellent biocompatibility and biodegradability, cell association, biological tissue culture, and biological activities, such as antibacterial, aromatic, non-toxic, and hemostatic properties (Park Jun-Kyu et al., 2015).

It is known that nucleic acids, which have been recognized as a genome to store and deliver genetic information, are distributed around the diseased tissue to promote cell growth and differentiation and angiogenesis and perform an inflammation inhibitory function. That is, nucleic acids are degraded into small fragments outside cells and bind to receptors on the cell surface to stimulate signals into the cells.

As for still another type of research, studies are being actively conducted in various fields, such as making very elaborate nanostructures using a self-assembly property inherent to nucleic acids. Since the formation results of hydrogels composed of DNA were reported in 2006 (Um S. H. et al., 2006), many groups have conducted studies about the formation of gels using DNA.

Hydrogels composed of DNA have very excellent biocompatibility, and thus are medically studied in various fields. The production results of functional DNA hydrogels that respond to heat and enzymes to induce free degradation and re-association have been recently reported (Xing Y. et al., 2011). Therefore, side effects due to overdosing of drugs can be reduced by enabling a smart drug delivery method in which drugs are allowed to flow only in case of necessity. Unlike existing hydrogel manufacturing methods using polymers, DNA hydrogels are composed of biomaterial DNA, and thus are not harmful to the human body, so the DNA hydrogels can be used as artificial tissues for wounded sites with various shapes and can be variously applied as an effective drug carrier in a medical field.

However, nucleic acids are easily degraded by degradation enzymes existing in the human body, so that the in vivo residence of nucleic acids for application of the nucleic acids to target disease tissues is low, resulting in a lack of drug persistence, and in the case where DNA hydrogels are utilized, the degradation of the nucleic acids by degradation enzymes causes a collapse of structures, and thus the DNA hydrogels may not properly perform as roles of artificial tissues and drug carriers (Lee Jong-beom, et al., 2012). Therefore, it is necessary to conduct research to enhance the drug persistence of nucleic acids and to solve the problems of DNA hydrogels.

The present inventors conducted continuous research in order to prepare a temperature-sensitive hydrogel, which exists in a sol state at room temperature and forms a gel when injected into the body, and as a result, the present inventors produced a temperature-sensitive hydrogel with biocompatibility and biodegradability through a combination of chitosan and a nucleic acid, and thus completed the present invention.

Korean Patent Publication No. 2014-0090670 as a prior art discloses an in-situ crosslinkable polymer composition, but never states temperature sensitivity and hydrogels. In addition, the crosslinkable polymer composition of this patent publication contains about 0.1 wt % to about 95 wt % of more than one kind of polyanionic polymer, about 0.1 wt % to about 90 wt % of more than one kind of polycationic polymer, and 0.1 wt % to 99.8 wt % of water, and thus this polymer composition is different from a temperature-sensitive hydrogel composition of the present invention in view of the mixing ratio. In addition, the patent publication discloses that the polyanions include crosslinkable and non-crosslinkable polyanions, and a polynucleotide is suggested as one of the non-crosslinkable polyanion components. However, the patent publication discloses that the non-crosslinkable polyanions are further included in the polyanions, and it can be seen that the non-crosslinkable anions do not influence crosslinkage. Whereas, a temperature-sensitive hydrogel of the present invention is formed through a non-crosslinkage between a nucleic acid and chitosan, and thus it can be seen that the temperature-sensitive hydrogel of the present invention is different from the polymer composition in the patent publication in view of the constituent elements. Furthermore, as a result of mixing 1 wt % of a nucleic acid and 0.1 wt % of chitosan with reference to the ratio supposed in Korean Patent Publication No. 2014-0090670, it was confirmed that opaque white precipitates were generated and after 3 days, the layer separation occurred.

European Publication Patent No. 2745849 discloses a combination of polydeoxyribonucleotide (PDRN) and chitosan but does not state a temperature-sensitive hydrogel, wherein the combination contains 0.002-0.25 wt % of polydeoxyribonucleotide and 1-10 wt % of chitosan, which is different from the constitution of the present invention.

In addition, US Patent Publication No. 2015-0111834 discloses an in-situ gel composition, wherein an anti-gelation agent is introduced for prevention of gelation at room temperature, and thus it can be seen that the in-situ gel composition is different from the constitution of the present invention.

DETAILED DESCRIPTION OF THE INVENTION

Technical Problem

An aspect of the present invention is to provide a temperature-sensitive hydrogel composition containing a nucleic acid and chitosan.

Technical Solution

In accordance with an aspect of the present invention, there is provided a temperature-sensitive hydrogel composition containing a nucleic acid and chitosan, wherein the weight ratio of the nucleic acid and the chitosan is 20:1 to 10000:1.

Preferably, the present invention may be a temperature-sensitive hydrogel composition wherein the weight ratio of a nucleic acid and chitosan is preferably 50:1 to 2000:1 and most preferably 100:1 to 1000:1.

The content of the nucleic acid may be 0.01 wt % to 3 wt % relative to the total weight of the composition.

The nucleic acid may be deoxyribonucleic acid (DNA), ribonucleic acid (RNA), or a mixture thereof.

The content of the chitosan may be $1 \times 10^{-6}$ wt % to 0.15 wt % relative to the total weight of the composition.

The molecular weight of the chitosan may be 3 kDa to 1000 kDa.

Furthermore, the temperature-sensitive hydrogel composition may contain a polymer material as an additional ingredient.

The polymer material may be at least one selected from the group consisting of hyaluronic acid, poly-γ-glutamic acid, cellulose, polyacrylic acid, polyamino acids, alginate, and derivatives and a combination thereof.

In accordance with another aspect of the present invention, there is provided a method for producing the temperature-sensitive hydrogel composition, the method including: i) preparing a nucleic acid stock solution; ii) preparing a chitosan stock solution; iii) mixing the nucleic acid stock solution in step i) and the chitosan stock solution in step ii) such that the weight ratio of a nucleic acid and chitosan is 20:1 to 10000:1, followed by stirring; and iv) lowering the nucleic acid-chitosan mixture liquid in step iii) to room temperature with stirring.

The method may include: i) putting a nucleic acid in a buffer solution, and dissolving the nucleic acid in the buffer solution for 1-2 hours with stirring at 60-70° C., to prepare a nucleic acid stock solution; ii) dissolving chitosan in an acidic buffer solution to prepare a chitosan stock solution; iii) mixing the nucleic acid stock solution in step i) and the chitosan stock solution in step ii) such that the weight ratio of the nucleic acid and the chitosan is 20:1 to 10000:1, followed by stirring at 55-65° C. for 1-2 hours; and vi) lowering the nucleic acid-chitosan mixture liquid in step iii) to room temperature with stirring.

The temperature-sensitive hydrogel composition may have an osmotic pressure of 100-500 mOsm and a pH value of 6-8.

Hereinafter, the present invention will be described in detail.

The temperature-sensitive hydrogel refers to a hydrogel of which a phase transition occurs from a sol into a gel or a gel into a sol according to the temperature. A transition of a sol into a gel is referred to as gelation. The gelation in the present invention is defined by a state in which a polymer having viscoelasticity forms a three-dimensional network structure with increasing temperature, and thus remains without being dissolved in a solvent.

In the temperature-sensitive hydrogel composition containing a nucleic acid and chitosan, the sol-gel transition temperature thereof may vary according to the mixing ratio of a nucleic acid and chitosan, and here, the sol-gel transition temperature can be adjusted by changing the mixing ratio according to the purpose for use.

The temperature-sensitive hydrogel composition containing a nucleic acid and chitosan is highly stable in which a homogeneous state is maintained and the layer separation does not occur. The weight ratio of the nucleic acid and the chitosan is in the range of preferably 20:1 to 10000:1, more preferably 50:1 to 2000:1, and most preferably 100:1 to 1000:1.

The content of the nucleic acid may be 0.01-3 wt %, preferably 0.1-2 wt %, and most preferably 1-1.5 wt % relative to the total weight of the composition.

The molecular weight of the nucleic acid may be 1-100,000 kDa, preferably 10-10,000 kDa, and most preferably 50-3,500 kDa.

The nucleic acid may be deoxyribonucleic acid (DNA), ribonucleic acid (RNA), or a mixture thereof. Preferably, the nucleic acid may be deoxyribonucleic acid.

In addition, the deoxyribonucleic acid may include oligonucleotides, polynucleotides, and polydeoxyribonucleotides (PDRN).

The nucleic acid may form a hydrogel through a combination with chitosan, and can act as a therapeutic drug in the body.

In addition, the content of chitosan may be $1\times10^{-6}$ wt % to 0.15 wt %, preferably $1\times10^{-5}$ wt % to 0.1 wt %, and most preferably $1\times10^{-4}$ wt % to 0.075 wt %, relative to the total weight of the composition.

The molecular weight of chitosan is 3 kDa to 1000 kDa, but is not limited thereto.

In addition, the temperature-sensitive hydrogel composition may contain a polymer material as an additional ingredient, wherein the polymer material may be added to make secure the adjustment of physical property changes according to the use of the temperature-sensitive hydrogel containing the nucleic acid and chitosan.

The polymer material may employ at least one selected from the group consisting poly-γ-glutamic acid, cellulose, poly amino acids, alginate, and of hyaluronic polyacrylic derivatives combination thereof, but is not limited thereto.

In addition, the temperature-sensitive hydrogel composition may be used for a medical use and as a cosmetic agent.

A method for producing the temperature-sensitive hydrogel includes: i) putting a nucleic acid in a buffer solution, and dissolving the nucleic acid in the buffer solution for 1-2 hours with stirring at 60-70° C., to prepare a nucleic acid stock solution; ii) dissolving chitosan in an acidic buffer solution to prepare a chitosan stock solution; iii) mixing the nucleic acid stock solution in step i) and the chitosan stock solution in step ii) such that the weight ratio of the nucleic acid and the chitosan is 20:1 to 10000:1, followed by stirring at 55-65° C. for 1-2 hours; and iv) lowering the nucleic acid-chitosan mixture liquid in step iii) to room temperature with stirring.

The buffer solution that can be used in the preparation of the nucleic acid stock solution may employ sodium phosphate dibasic dodecahydrate, sodium chloride, magnesium chloride, potassium chloride, phosphate buffer saline, or HEPES (N-(2-hydroxyethyl)-piperazine-N'-2-ethanesulfonic acid) buffer solution, and preferably sodium phosphate dibasic dodecahydrate, but is not limited thereto.

The acidic buffer that can be used in the preparation of the chitosan stock solution may employ acetic acid, hydrochloric acid, ascorbic acid, lactic acid, and nitric acid, and preferably acetic acid, but is not limited thereto.

The mixing of the nucleic acid and the chitosan is conducted such that the weight ratio of nucleic acid and chitosan is 20:1 to 10000:1, and here, the content of the nucleic acid is 0.01-3 wt % relative to the total weight of the composition, and the content of the chitosan is $1\times10^{-6}$ wt % to 0.15 wt % relative to the total weight of the composition.

As for the temperature-sensitive hydrogel composition obtained by the production method, the osmotic pressure and pH thereof may be adjusted so that the composition can be injected into the human body or coated on the skin.

For adjustment of pH of the temperature-sensitive hydrogel composition obtained by the production method, the production method may further include a step of adjusting pH in step iv).

The osmotic pressure of the temperature-sensitive hydrogel composition obtained by the production method may be 100-500 mOsm, preferably 150-450 mOsm, and most preferably 200-400 mOsm.

The pH of the temperature-sensitive hydrogel composition obtained by the production method may be 6-8, preferably 6.5-7.5, and most preferably 7.

Advantageous Effects

The present invention provides a temperature-sensitive hydrogel composition containing a nucleic acid and chitosan. The hydrogel has excellent biocompatibility and biostability and exhibits a sol-gel transition property according to the temperature change, so that the hydrogel exists in a sol state at room temperature, and the hydrogel is gelated when the hydrogel has a high temperature by being injected into the body or coated on the epidermal skin surface.

Therefore, the temperature-sensitive hydrogel of the present invention can be directly injected and coated on a particular site in needed of therapy, and can increase the time for drug persistence and drug attachment through the gelation according to the temperature, and thus the drug efficacy thereof can sufficiently exerted. Therefore, the temperature-sensitive hydrogel is expected to be utilized in various therapies.

MODE FOR CARRYING OUT THE INVENTION

Figure 1:
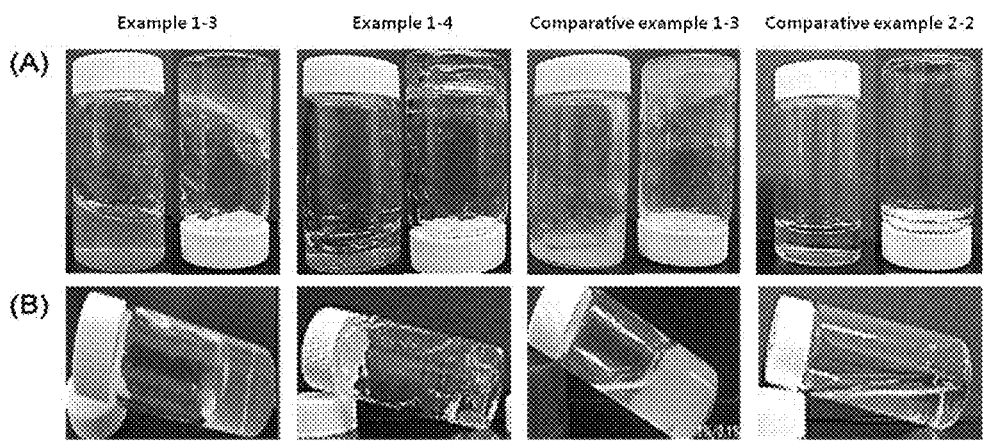
FIG. 1 shows the results of confirming physical property states of temperature-sensitive hydrogels according to the mixing ratio of a nucleic acid and chitosan. Each composition was subjected to mixing, and then was investigated for transparency and viscoelasticity (A) and precipitate generation and layer separation (B) for 3 days.

Hereinafter, preferable embodiments of the present invention will be described in detail. However, the present invention is not limited to the embodiments described herein but may be embodied in other forms. Rather, these embodiments are provided so that this disclosure will be thorough and complete, and will fully convey the scope of the invention to those skilled in the art.

Example 1

Production of Nucleic Acid-Chitosan Hydrogels

For the production of nucleic acid and chitosan hydrogels, nucleic acid and chitosan stock solutions were prepared with concentrations corresponding examples shown in table 1 below. Here, nucleic acid was put in a buffer solution of 200 mM sodium phosphate dibasic dodecahydrate, and then dissolved therein using a heat stirrer at 65° C. for 1 hour.

In addition, chitosan was dissolved using 100 mM acetic acid.

The nucleic acid and chitosan stock solutions prepared with the concentrations in table 1 below were mixed at a weight ratio of 1:1, and stirred in a heat stirrer at 60° C. for 1 hour. Thereafter, the temperature was lowered to room temperature, followed by stirring for 1 hour, to produce nucleic acid-chitosan hydrogels.

Comparative Example 1

Production of Comparative Nucleic Acid-Chitosan Hydrogel

Nucleic acid and chitosan stock solutions were prepared with concentrations corresponding to comparative examples shown in table 1 below. Comparative nucleic acid-chitosan hydrogels were produced by the same method as in example 1.

TABLE 1

| Constitution | Stock solution concentration (wt %) | | Final concentration (wt %) | |
|---|---|---|---|---|
| | Nucleic acid | Chitosan | Nucleic acid | Chitosan |
| Example 1-1 | 2 | 0.1 | 1 | 0.05 |
| Example 1-2 | 2 | 0.04 | 1 | 0.02 |
| Example 1-3 | 2 | 0.02 | 1 | 0.01 |
| Example 1-4 | 2 | 0.002 | 1 | 0.001 |
| Example 1-5 | 2 | 0.001 | 1 | 0.0005 |
| Example 1-6 | 2 | 0.0004 | 1 | 0.0002 |
| Example 1-7 | 2 | 0.0002 | 1 | 0.0001 |
| Example 1-8 | 0.02 | 0.0002 | 0.01 | 0.0001 |
| Example 1-9 | 0.02 | 0.00002 | 0.01 | 0.00001 |
| Example 1-10 | 6 | 0.06 | 3 | 0.03 |
| Example 1-11 | 6 | 0.006 | 3 | 0.003 |
| Comparative example 1-1 | 2 | 0 | 1 | 0 |
| Comparative example 1-2 | 0 | 0.02 | 0 | 0.01 |
| Comparative example 1-3 | 2 | 0.2 | 1 | 0.1 |
| Comparative example 1-4 | 2 | 0.0001 | 1 | 0.00005 |

Example 2

Production of Nucleic Acid-Chitosan-Hyaluronic Acid Hydrogel

A nucleic acid-chitosan-hyaluronic acid hydrogel was produced through the following procedure.

A nucleic acid was dissolved in a buffer solution of 200 mM sodium phosphate dibasic dodecahydrate to have a concentration of 2.2 wt %. Here, the nucleic acid were dissolved using a heat stirrer at 65° C. for 1 hour.

In addition, chitosan was dissolved in 100 mM acetic acid to have a concentration of 0.4 wt %.

Sodium hyaluronic acid was dissolved in a buffer solution of 200 mM sodium phosphate dibasic dodecahydrate to have a concentration of 2 wt %. Here, the sodium hyaluronic acid was dissolved using a heat stirrer at 40° C. for 30 minutes, followed by cooling to room temperature with stirring using a stirrer.

Then, 2.2 wt % of the prepared nucleic acid solution and 0.4 wt % of the prepared chitosan solution were mixed at a weight ratio of 9:1, followed by stirring in a heat stirrer at 65° C. for 10 minutes. 2 wt % of sodium hyaluronic acid was added to the nucleic acid-chitosan mixture solution at a weight ratio of 1:1, followed by stirring in a heat stirrer at 65° C. for 1 hour, and then the resulting solution was cooled to room temperature while the stirring maintained, thereby producing nucleic acid-chitosan-hyaluronic acid hydrogels of example 2.

Comparative Example 2

Production of Comparative Chitosan-Hyaluronic Acid Hydrogel

Chitosan and hyaluronic acid stock solutions were prepared with concentrations in table 2 below.

Chitosan was dissolved using 100 mM acetic acid.

Sodium hyaluronic acid was dissolved in a buffer solution of 200 mM sodium phosphate dibasic dodecahydrate. Here, sodium hyaluronic acid was dissolved using a heat stirrer at 40° C. for 30 minutes, and then the resulting solution was cooled to room temperature while the stirring was maintained. The prepared chitosan and hyaluronic acid solutions were mixed at a weight ratio of 1:1, followed by stirring in a heat stirrer at 65° C. for 1 hour. Thereafter, the temperature was lowered to room temperature, followed by stirring for 1 hour, to produce chitosan-hyaluronic acid hydrogels.

TABLE 2

| Constitution | Stock solution concentration (wt %) | | Final concentration (wt %) | |
|---|---|---|---|---|
| | Chitosan | Hyaluronic acid | Chitosan | Hyaluronic acid |
| Comparative example 2-1 | 0 | 2 | 0 | 1 |
| Comparative example 2-2 | 0.02 | 2 | 0.01 | 1 |

Experimental Example 1

Confirmation of Physical Properties of Nucleic Acid-Chitosan Hydrogels

The hydrogel compositions of example 1, example 2, comparative example 1, and comparative example 2 were used to investigate gelation, gel stability, and solubility thereof.

Each composition was subjected to mixing, and then the transparency and gelation state thereof were observed to the naked eye for 3 days. The gelation was examined by viscoelasticity and the gel stability was examined by precipitate generation and layer separation.

For the solubility of gel, the hydrogel composition of each of example 1, example 2, comparative example 1, and comparative example 2 was dropped in an aqueous solution at 37.5° C., followed by gelation, and then the solubility of gel was examined while the stirring was conducted at 400 rpm for 5 minutes with the temperature maintained at 37.5° C. The results were shown in table 3 and FIGS. 1 and 2.

TABLE 3

| Constitution | Results after three days | | | Results of stirring at 37.5° C. for 5 minutes Gel solubility |
|---|---|---|---|---|
| | Viscoelasticity | Precipitate generation | Layer separation | |
| Example 1-1 | ○ | X | X | X |
| Example 1-2 | ○ | X | X | X |
| Example 1-3 | ○ | X | X | X |
| Example 1-4 | ○ | X | X | X |
| Example 1-5 | ○ | X | X | X |
| Example 1-6 | ○ | X | X | X |
| Example 1-7 | ○ | X | X | X |
| Example 1-8 | ○ | X | X | X |
| Example 1-9 | ○ | X | X | X |
| Example 1-10 | ○ | X | X | X |
| Example 1-11 | ○ | X | X | X |
| Example 2 | ○ | X | X | X |
| Comparative example 1-1 | ○ | X | X | ○ |
| Comparative example 1-2 | X | X | X | ○ |
| Comparative example 1-3 | ○ | ○ | ○ | ○ |
| Comparative example 1-4 | ○ | ○ | X | ○ |
| Comparative example 2-1 | X | X | X | ○ |
| Comparative example 2-2 | ○ | X | X | ○ |

It can be seen from table 3 and FIG. 1 that, in the temperature-sensitive hydrogel compositions of examples 1-1 to 1-11, the precipitate isolation and the layer separation did not occur with viscoelasticity maintained, even three days after the nucleic acid and chitosan were mixed. However, as for comparative examples 1-1 to 1-4, which got out of the weight ratio range of nucleic acid and chitosan of the present invention, the precipitate generation, the layer separation, or the viscoelasticity was not observed.

Figure 2:
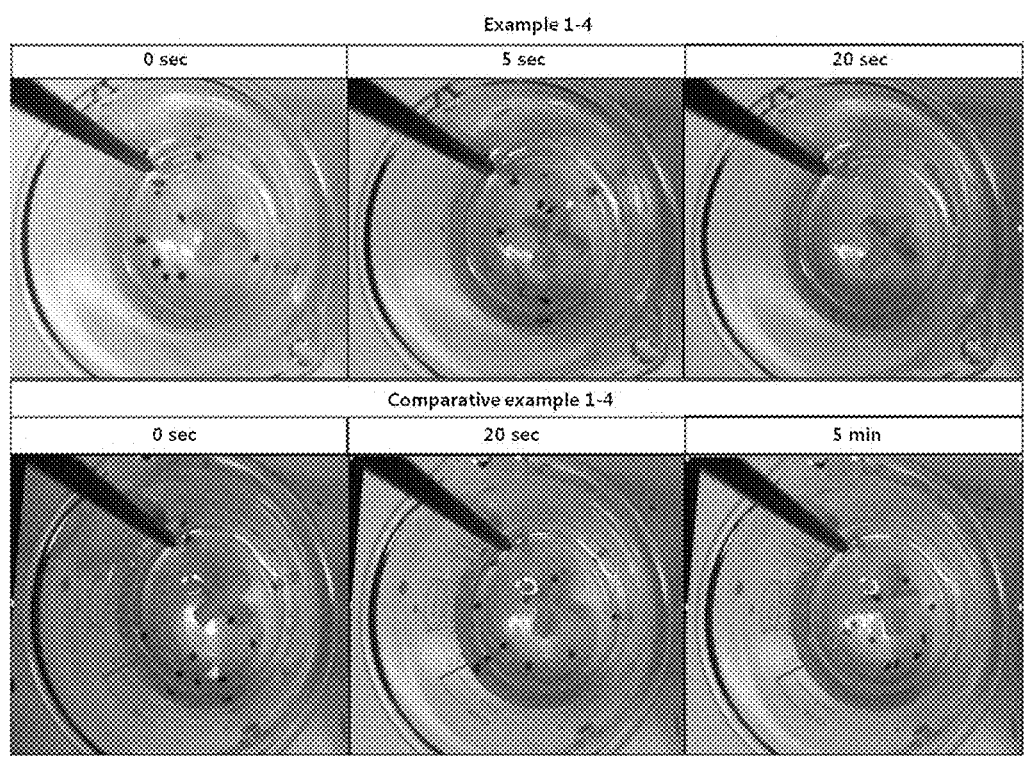
FIG. 2 shows the results of confirming whether gels are dissolved.

In addition, it can be seen from the solubility of gel in table 3 and FIG. 2 that the temperature-sensitive hydrogel composition of each of examples 1-1 to 1-11 formed a gel at 37.5° C. and the formed gel was continuously maintained, whereas comparative examples 1-1 to 1-4 were not gelated at 37.5° C. or were completely dissolved within 20 seconds even if the gelation occurred.

It was confirmed that, even in example 2 in which hyaluronic acid as an additional ingredient was added in the nucleic acid and chitosan, the viscoelasticity was maintained even while the precipitate isolation and the layer separation were not shown and the gel was continuously maintained after the gelation, whereas in comparative example 2-2 in which the nucleic acid was not contained, the precipitate isolation and the layer separation were not shown with viscoelasticity maintained, but the gel was dissolved within 20 seconds after the gel was formed at 37.5° C. (see table 3 and FIG. 1).

Through these results, it can be seen that the hydrogel composition of the present invention shows temperature sensitivity, high stability, and a gel form continuously maintained after gelation, and here, it was confirmed that the weight ratio of nucleic acid and chitosan plays a key role.

Experimental Example 2

Confirmation of Sol-Gel Transition with Temperature

The temperature-sensitive hydrogel composition produced in each of example 1, example 2, comparative example 1, and comparative example 2 was examined for sol-gel transition.

For the confirmation of sol-gel transition, a rheometer was used. The measurement conditions used here were PU20, gap of 0.5 mm, 0.1 Hz, and 1% stress-strain, and the changes of G' (elasticity) and G" (viscosity) were measured while the temperature was raised from 24° C. to 40° C. by 1° C. and then was maintained for 1 minute. In addition, the sol-gel transition after and before 36° C. was observed to the naked eye while the temperature of each composition was raised, and the results were shown in FIG. 3.

Figure 3:
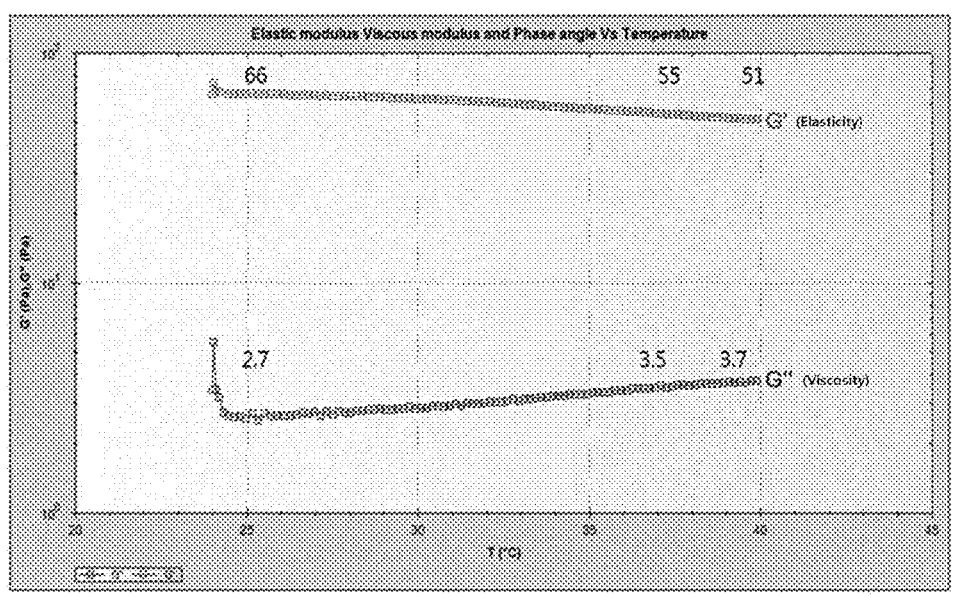
FIG. 3 shows the results of confirming the sol-gel transition of a temperature-sensitive hydrogel composition.
Figure 3:
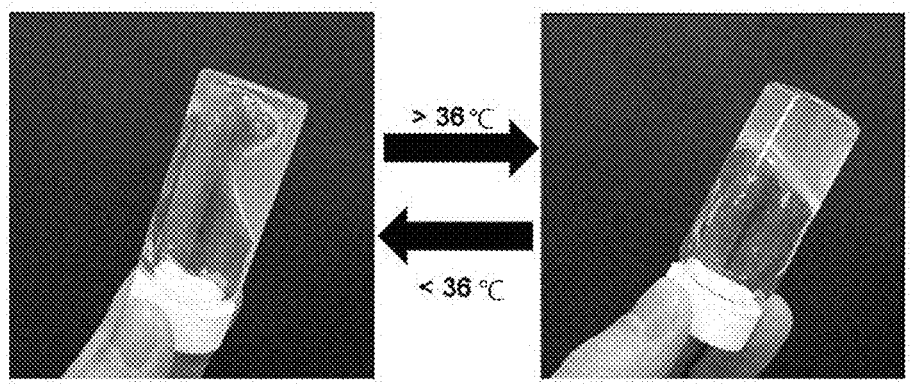

As shown in FIG. 3, it was observed that the temperature-sensitive hydrogel of example 1-3 exhibited a gentle decrease width of G' (elasticity) and an increase of G" (viscosity) with an increasing temperature (FIG. 3A), which correspond to the feature of a temperature-sensitive hydrogel. In addition, it was observed that the temperature-sensitive hydrogel of example 1-3 exhibited a sol state at a temperature lower than 36° C. but was gelated at a temperature exceeding 36° C. (FIG. 3B). It was confirmed that these results were identical in all of the temperature-sensitive hydrogel compositions in examples 1 and 2. It can be seen from these results that the hydrogel compositions of the present invention show temperature sensitivity.

The invention claimed is:

1. A temperature-sensitive hydrogel composition comprising a nucleic acid and chitosan,
   wherein the content of the nucleic acid is 1 wt % to 3 wt % relative to the total weight of the composition, wherein the content of the chitosan is 0.001 wt % to 0.03 wt % relative to the total weight of the composition, wherein the weight ratio of the nucleic acid and the chitosan is 33.333:1 to 3000:1, and
   wherein the temperature-sensitive hydrogel composition has a pH value of 6-8.

2. The temperature-sensitive hydrogel composition of claim 1, wherein the weight ratio of the nucleic acid and the chitosan is 50:1 to 2000:1.

3. The temperature-sensitive hydrogel composition of claim 2, wherein the weight ratio of the nucleic acid and the chitosan is 100:1 to 1000:1.

4. The temperature-sensitive hydrogel composition of claim 1, wherein the content of the nucleic acid is 1-2 wt % relative to the total weight of the composition.

5. The temperature-sensitive hydrogel composition of claim 1, wherein the nucleic acid is deoxyribonucleic acid (DNA), ribonucleic acid (RNA), or a mixture thereof.

6. The temperature-sensitive hydrogel composition of claim 1, wherein the content of the chitosan is 0.003 wt % to 0.02 wt % relative to the total weight of the composition.

7. The temperature-sensitive hydrogel composition of claim 6, wherein the molecular weight of the chitosan is 3 kDa to 1,000 kDa.

8. The temperature-sensitive hydrogel composition of claim 1, wherein the temperature-sensitive hydrogel composition contains a polymer material as an additional ingredient.

9. The temperature-sensitive hydrogel composition of claim 8, wherein the polymer material is at least one selected from the group consisting of hyaluronic acid, poly-γ-glutamic acid, cellulose, polyacrylic acid, polyamino acids, alginate, and a combination thereof.

10. A method for producing the temperature-sensitive hydrogel composition of claim 1, the method comprising: i) dissolving the nucleic acid in a buffer solution for 1-2 hours with stirring at 60-70° C., to prepare a nucleic acid stock solution; ii) dissolving chitosan in an acidic buffer solution to prepare a chitosan stock solution; iii) mixing together the nucleic acid stock solution in step i) and the chitosan stock solution in step ii) such that the weight ratio of the nucleic acid and the chitosan is 33.333:1 to 3000:1, followed by stirring at 55-65° C. for 1-2 hours; and iv) lowering the nucleic acid-chitosan mixture liquid in step iii) to room temperature with stirring, thereby obtaining the temperature-sensitive hydrogel composition comprising a nucleic acid and chitosan.

11. The method of claim 10, wherein the temperature-sensitive hydrogel composition has an osmotic pressure of 100-500 mOsm.

12. The method of claim 10, wherein the temperature-sensitive hydrogel composition has a pH value of 6.5-7.5.

13. The method of claim 10, wherein the weight ratio of the nucleic acid and the chitosan is 50:1 to 2000:1.

14. The method of claim 13, wherein the weight ratio of the nucleic acid and the chitosan is 100:1 to 1000:1.

15. The method of claim 10, wherein the content of the nucleic acid is 1-3 wt % relative to the total weight of the composition.

16. The method of claim 10, wherein the nucleic acid is deoxyribonucleic acid (DNA), ribonucleic acid (RNA), or a mixture thereof.

17. The method of claim 10, wherein the content of the chitosan is 0.001 wt % to 0.03 wt % relative to the total weight of the composition.

18. The method of claim 10, wherein the molecular weight of the chitosan is 3 kDa to 1,000 kDa.

19. The method of claim 10, wherein the temperature-sensitive hydrogel composition contains a polymer material as an additional ingredient.

* * * * *